US008456725B2

(12) United States Patent
Toomre et al.

(10) Patent No.: US 8,456,725 B2
(45) Date of Patent: Jun. 4, 2013

(54) OPTICAL SYSTEM THAT SELECTIVELY PROVIDES EITHER OF A COLLIMATED LIGHT BEAM OR A CONVERGENT LIGHT BEAM

(75) Inventors: Derek Kalev Toomre, New Haven, CT (US); Vladimir Ivanovich Polejaev, Middletown, CT (US); Robert Dixon Roorda, Oxford (GB)

(73) Assignee: Yale University, New Haven, CT (US)

( * ) Notice: Subject to any disclaimer, the term of this patent is extended or adjusted under 35 U.S.C. 154(b) by 309 days.

(21) Appl. No.: 12/866,314

(22) PCT Filed: Mar. 25, 2009

(86) PCT No.: PCT/US2009/001868
§ 371 (c)(1),
(2), (4) Date: Dec. 7, 2010

(87) PCT Pub. No.: WO2009/120336
PCT Pub. Date: Oct. 1, 2009

(65) Prior Publication Data
US 2011/0069382 A1    Mar. 24, 2011

(51) Int. Cl.
*G02B 26/08* (2006.01)
(52) U.S. Cl.
USPC ...................................... 359/201.2
(58) Field of Classification Search
USPC .......................................... 359/201.1, 201.2
See application file for complete search history.

(56) References Cited

U.S. PATENT DOCUMENTS

| | | | |
|---|---|---|---|
| 6,924,490 B2 * | 8/2005 | Natori | 250/458.1 |
| 7,042,638 B2 | 5/2006 | Gonschor et al. | 359/385 |
| 7,050,208 B2 * | 5/2006 | Overbeck | 359/201.1 |
| 7,170,676 B2 | 1/2007 | Aono | 359/388 |
| 7,551,351 B2 | 6/2009 | Ulrich et al. | |
| 7,573,635 B2 | 8/2009 | Uhl | |

FOREIGN PATENT DOCUMENTS

| | | |
|---|---|---|
| DE | 10 2006 028530 | 5/2007 |
| JP | 2003-270538 | 8/2012 |
| WO | 2005/031428 | 4/2005 |

OTHER PUBLICATIONS

International Search Report and Written Opinion dated May 28, 2009 for corresponding International Application No. PCT/US2009/001868.
International Preliminary Report on Patentability Dated May 30, 2012 From Corresponding International Application No. PCT/US2009/01868.

(Continued)

*Primary Examiner* — Euncha Cherry
(74) *Attorney, Agent, or Firm* — Ohlandt, Greeley, Ruggiero & Perle, L.L.P.

(57) ABSTRACT

There is provided a method that includes projecting a collimated light beam from an optical system to a plane during a first mode of operation of the optical system, and projecting a convergent light beam from the optical system to the plane during a second mode of operation of the optical system. The method further includes, (a) during the first mode of operation, controlling a trajectory of a first light bundle in a first light path in the optical system, to steer the collimated light beam through the plane at a designated incidence angle, and (b) during the second mode of operation, controlling a trajectory of a second light bundle in a second light path of the optical system, to steer the convergent light beam to a target position in the plane. There is also provided an apparatus and a system that employs the method.

21 Claims, 9 Drawing Sheets

OTHER PUBLICATIONS

Supplementary Partial European Search Report Dated Mar. 27, 2012 From Corresponding European Application No. EP 09 72 4592.
Notification of Reasons for Refusal Dated Aug. 24, 2012 From Corresponding Japanese Application No. JP2011-501806.
Fiolka, R., et al., *Even Illumination in Total Internal Reflection Fluorescence Microscopy Using Laser Light*, Microscopy Research and Technique 71:45-50 (2008).
Mattheyses, Alexa L., et al., *Effective Elimination of Laser Interference Fringing in Fluorescence Microscopy by Spinning Azimuthal Incidence Angle*, Microscopy Research and Technique 69:642-647 (2006).
Yang, Q., et al., *Estimation of 3D Geometry of Microtubules Using Multi-Angle Total Internal Reflection Fluorescence Microscopy* (*abstract only*), Med Image Comput Assist Intery 13(Pt 2):538-45 (2010)—http://www.ncbi.nlm.nih.gov/pubmed/20879357.
*Reflection Fluorescence Microscopy* (*abstract only*), Med Image Comput Assist Interv 13(Pt 2):538-45 (2010)-http://www.ncbi.nlm.nih.gov/pubmed/20879357.

* cited by examiner

U.S. 8,456,725 B2

OPTICAL SYSTEM THAT SELECTIVELY PROVIDES EITHER OF A COLLIMATED LIGHT BEAM OR A CONVERGENT LIGHT BEAM

GOVERNMENT LICENSE RIGHTS

This invention was made with government support under OD002980 awarded by the National Institute of Health. The government has certain rights in the invention.

BACKGROUND OF THE INVENTION

1. Field of the Invention

The present disclosure relates to illumination systems, and more specifically, to an illumination system that selectively provides either of a collimated light beam or a convergent light beam. The system is particularly well-suited where illumination is desired for both total internal reflection fluorescent (TIRF) microscopy and fluorescence recovery after photobleaching (FRAP) or photoactivation experiments.

2. Description of the Related Art

The approaches described in this section are approaches that could be pursued, but not necessarily approaches that have been previously conceived or pursued. Therefore, unless otherwise indicated, the approaches described in this section may not be prior art to the claims in this application and are not admitted to be prior art by inclusion in this section.

A fluorescence microscope is a light microscope used to study properties of organic or inorganic substances using the phenomena of fluorescence and phosphorescence instead of, or in addition to, reflection and absorption. In some cases, for example, fluorescence recovery after photobleaching (FRAP), an image plane of a microscope is best illuminated by a converging beam of light. In other cases, for example, total internal reflection fluorescence (TIRF), the image plane is best illuminated by a collimated beam of light.

SUMMARY OF THE INVENTION

There is provided a method that includes projecting a collimated light beam from an optical system to a plane during a first mode of operation of the optical system, and projecting a convergent light beam from the optical system to the plane during a second mode of operation of the optical system. The method further includes, (a) during the first mode of operation, controlling a trajectory of a first light bundle in a first light path in the optical system, to steer the collimated light beam through the plane at a designated incidence angle, and (b) during the second mode of operation, controlling a trajectory of a second light bundle in a second light path of the optical system, to steer the convergent light beam to a target position in the plane. There is also provided an apparatus and a system that employs the method.

DESCRIPTION OF THE INVENTION

A component or a feature that is common to more than one drawing is indicated with the same reference number in each of the drawings.

Figure 1:
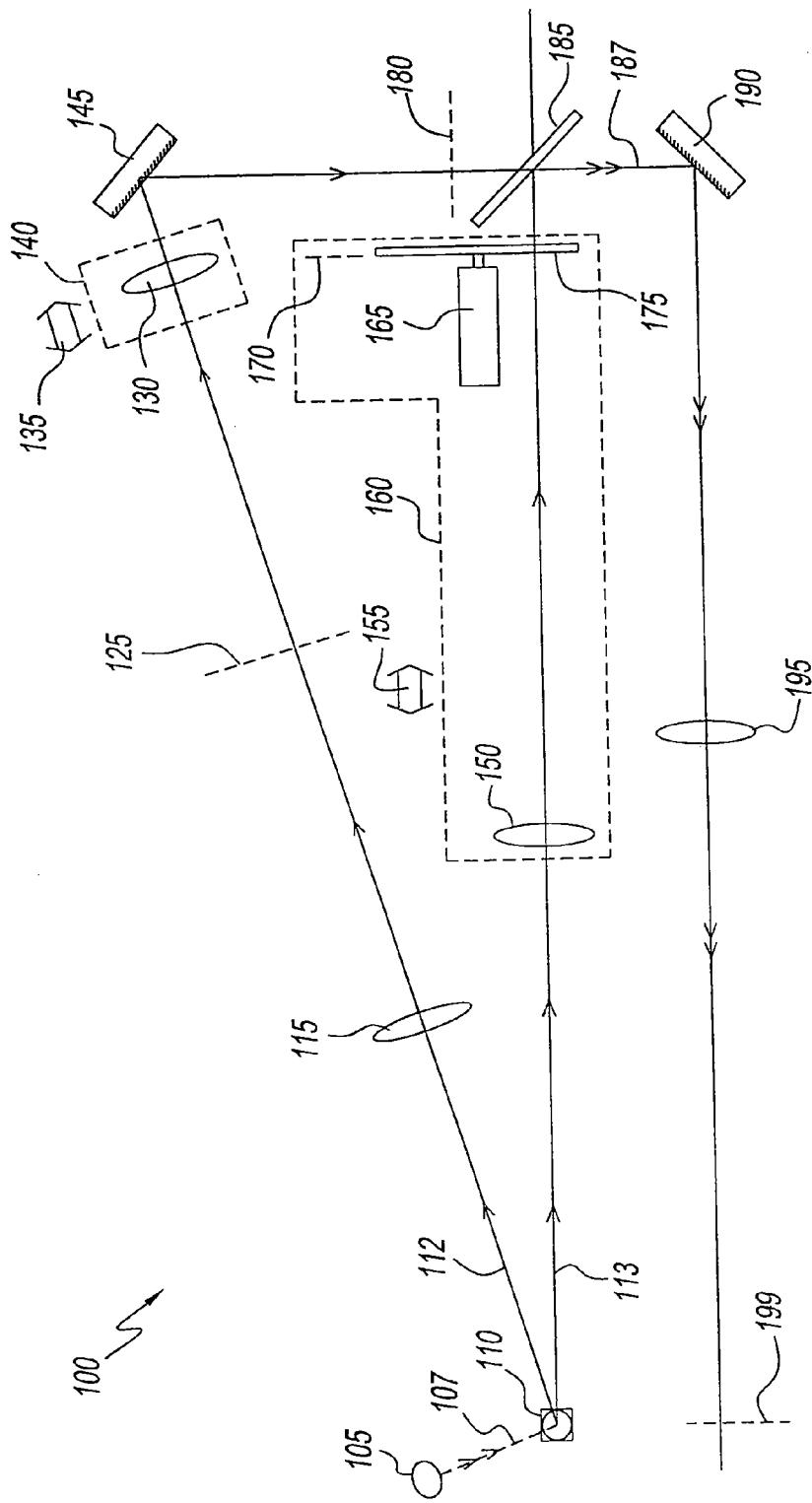
FIG. 1 is a block diagram of an illumination system.

FIG. 1 is a block diagram of an illumination system, i.e., a system 100, that has a mode of operation that projects a collimated light beam to a plane 199, and a mode of operation that projects a convergent light beam to plane 199. For convenience, we refer to the mode of operation that projects the collimated light beam to plane 199 as "collimated mode", and we refer to the mode of operation that projects the convergent light beam to plane 199 as "convergent mode."

System 100 includes a light source 105, a light steering device 110, lenses 115, 130, 150 and 195, mirrors 145 and 190, a diffuser 175, and a light steering device 185.

Light source 105 emits a light beam 107. Light source 105 may be implemented as a laser, for example, and preferably emits light beam 107 as a collimated beam.

Light steering device 110 receives light beam 107 from light source 105. Light source 105 may be coupled to light steering device 110 with a fiber optic cable (not shown) and a collimator (not shown), but it can also be directly coupled using mirrors (not shown).

Light steering device 110 selectively directs the light to one of two light paths generally designated as light path 112 and light path 113, and more particularly, directs the light to light path 112 for convergent mode, and directs the light to light path 113 for collimated mode. Light steering device 110 may include, for example, a galvanometer scanning mirror or an acousto-optical deflector.

Light path 112 runs from light steering device 110, through lens 115, through lens 130, to mirror 145, and then to light steering device 185. Light path 113 runs from light steering device 110, through lens 150, through diffuser 175, and then to light steering device 185.

Light steering device 185 receives the light via either light path 112, from mirror 145, or via light path 113, from diffuser 175, and emits the light to a downstream light path, i.e., a light path 187. Light steering device 185 may include, for example, an elliptical zone mirror (EZM), an elliptical mirror, a round mirror, a mirror having a clear aperture, a beam combiner, a beam splitter, a beam cube, or a polarizing beam cube. Light path 187 runs from light steering device 185, to mirror 190, through lens 195, and then to plane 199.

In convergent mode, the light propagates via light paths 112 and 187, and system 100 produces the convergent light beam in plane 199. In collimated mode, the light propagates via light paths 113 and 187, and system 100 produces the collimated light beam in plane 199.

An angle at which light steering device 110 directs the light to light path 112 or to light path 113 influences an angle at which the light arrives at plane 199. In convergent mode, by controlling a trajectory of the light into light path 112, light steering device 110 steers the convergent light beam to a target position in plane 199. In collimated mode, by controlling a trajectory of the light into light path 113, light steering device 110 steers the collimated light beam through plane 199 at a designated incidence angle.

For two-dimensional, i.e., x-direction and y-direction, steering of the light, light steering device 110 may be implemented as an orthogonal pair of galvanometer scanning mirrors or a dual axis acousto-optical deflector. Galvanometer scanning mirrors have a response time of less than a millisecond, and can therefore be used for small beam apertures and moderate angular steps. Thus, galvanometer scanning mirrors can rapidly move light beam 107 to a specified exit angle coordinate. Depending on the exit angle specified by the light steering device 110 the system 100 can illuminate either a focused spot, i.e., the target position, within plane 199, or can project a collimated beam through plane 199 at the designated incident angle. Also, if no other means of beam modulation is available, and if desired, light steering device 110 could be used to block light beam 107 by directing it to a beam stop (not shown).

System 100 can be employed as an illumination system for a microscope, where plane 199 coincides with an image plane of the microscope. Collimated mode can be employed in conjunction with processes such as (a) total internal reflection fluorescent illumination, and (b) evanescent field fluorescence recovery after photobleaching illumination. Convergent mode can be employed in conjunction with processes such as (a) fluorescence recovery after photobleaching illumination, (b) photoactivation illumination, (c) photobleaching illumination, (d) an optical tweezers operation, and (e) an optical uncaging operation.

Utilizing a shared source beam and a shared two-axis beam steering device, system 100 creates two different illumination conditions at a common destination plane, i.e., plane 199: Incidence angle addressable collimated illumination and position addressable focal illumination.

In collimated mode, system 100 directs the collimated beam through the center of plane 199. In this mode the angular direction coordinates of the collimated beam exiting light steering device 110 determine the incidence direction of the collimated beam intersecting plane 199.

In convergent mode, system 100 directs the converging beam of light to a focal spot in plane 199. In this mode the angular direction coordinates of a collimated beam exiting light steering device 110 determine the lateral position of the focal spot within plane 199.

The mode of operation is determined by selection with light steering device 110, of the corresponding range of angular direction coordinates. The angular ranges applicable to each mode of operation are non-overlapping. Light steering device 110 is controlled electronically, and may utilize feedback and analysis to optimize the resultant illumination.

For convenience, below, we are using the phrase "light bundle" to designate a segment of light.

Figure 2:
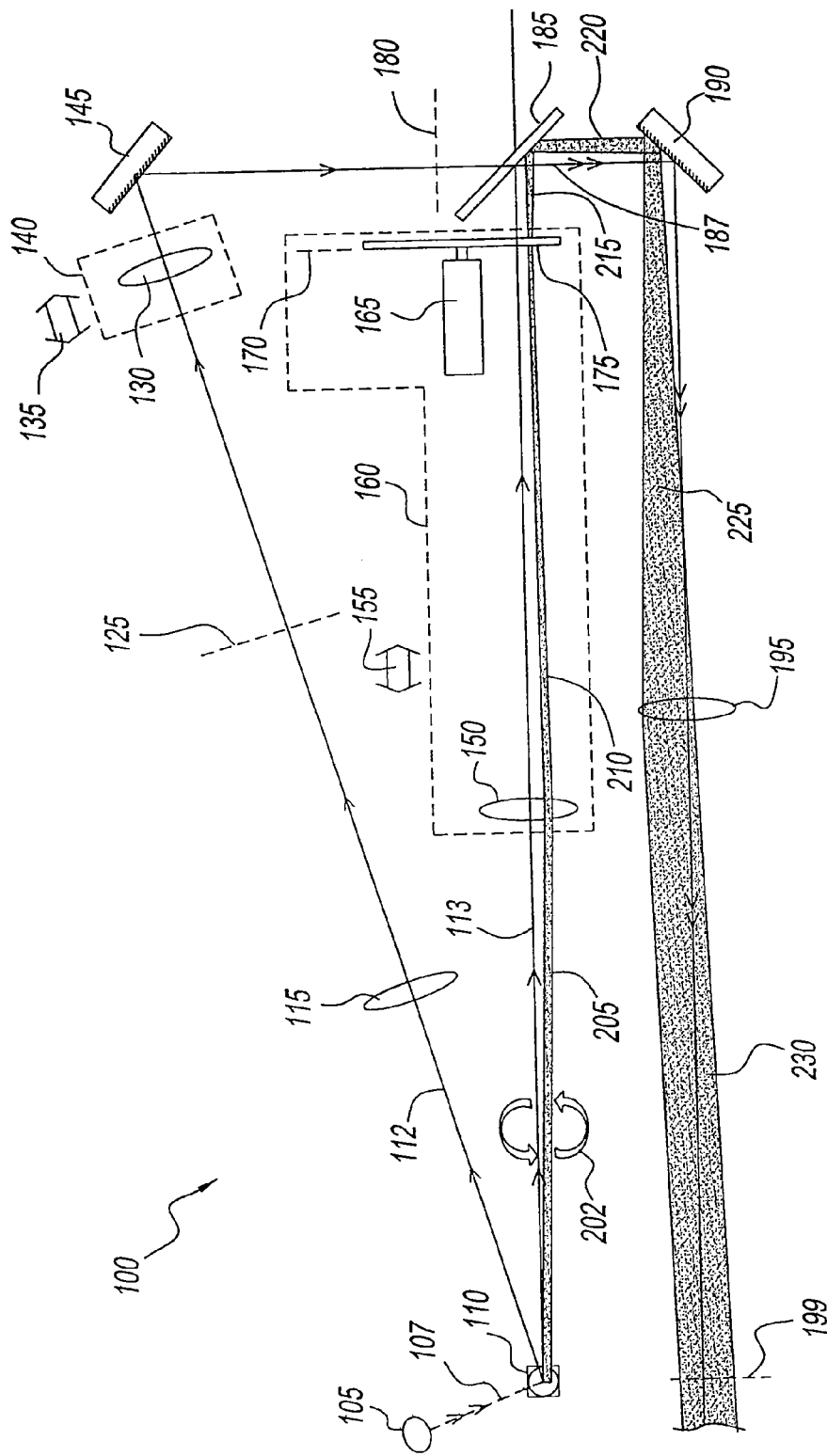
FIG. 2 is an illustration of the operation of the system of FIG. 1 in a mode of operation that projects a collimated light beam to a plane.

FIG. 2 is an illustration of the operation of system 100 in collimated mode. In collimated mode, light steering device 110 receives a light bundle from light source 105 and directs the light bundle to light path 113. The light bundle propagates (a) from light steering device 110 to lens 150 in a collimated beam 205, (b) through lens 150 to diffuser 175 in a convergent beam 210, (c) through diffuser 175 to light steering device 185 in a divergent beam 215, (d) from light steering device 185 to mirror 190 in a divergent beam 220, (e) from mirror 190 to lens 195 in a divergent beam 225, and (f) from lens 195 to plane 199 in a collimated beam 230.

Lens 150 focuses collimated beam 205 onto diffuser 175 as convergent beam 210. Diffuser 175 is situated at a plane 170 and rotated by a rotator 165. Diffuser 175 creates an even illumination by collimated beam 230 in plane 199. Lens 150 and diffuser 175 may be regarded as an optical subsystem that transforms the light bundle so that the light bundle is projected to plane 199 in collimated beam 230. Light steering device 185 receives the light bundle in divergent beam 215, and directs the light bundle to mirror 190 in divergent beam 220. Mirror 190 reflects, and thus directs, the light bundle to lens 195 in divergent beam 225. Lens 195 receives the light bundle in divergent beam 225, and projects the light bundle, in collimated beam 230. Light steering device 110 controls a trajectory of the light bundle in light path 113 to steer collimated beam 230 through plane 199 at a designated incident angle.

In collimated mode, light steering device 110 and plane 199 are located at the pupils of a telescope formed by lenses 150 and 195. Thus, any beam being projected by light steering device 110 will be centered on the intersection of plane 199 and the optic axis. It is the approach angle with respect to the optic axis that is varied by small deflections near path 113 that are relayed by the optics to plane 199.

The distance from light steering device 110 to lens 150 is equal to the focal length of lens 150, and so, the convergent beam into plane 170 is telecentric. The distance between diffuser 175 and lens 195 equals the focal length of lens 195, resulting in telecentric motion of the collimated beam along path 230 and a stationary intersection of the collimated beam at the center of plane 199.

The collimation of collimated beam 230 can be adjusted, as indicated by an arrow 155, by moving lens 150 and diffuser 175, which are mounted on a common translation mount 160 for this purpose.

When system 100 is being employed with a microscope, it is configured such that plane 199, i.e., the exit plane, is located coincident with a conjugate plane to the focal plane of the microscope objective lens. The objective lens focal plane is often called the specimen plane and it is the in-focus plane of a specimen that is imaged by the microscope. The conjugate plane is generally a magnification of the microscope objective focal plane.

Collimated beams incident on the conjugate plane are relayed through the microscope intermediate optics and the microscope objective lens and exit as collimated beams through the microscope objective lens focal plane. Thus to obtain a desired collimated beam exit direction from the microscope objective the appropriate beam direction about the collimated light path 113 is selected.

TIRF microscopy is used to image a thin section of a specimen by utilizing the very thin evanescent field created when an interface between a high optical index material and a low optical index material is illuminated at an incidence angle greater than the critical angle (the angle of total internal reflection). This illumination condition is called illumination at a supercritical angle of incidence or simply supercritical illumination.

In a typical 'through the objective' TIRF microscope arrangement, a specimen of interest is placed on a thin glass cover-slip that is placed in the focal plane of a microscope objective with the specimen on the surface facing away from the microscope objective. The cover-slip is illuminated with collimated light at a supercritical angle to create the thin evanescent field along the surface of the cover-slip facing away from the microscope objective.

To create the illumination conditions for TIRF microscopy with the system 100 coupled to a microscope, the appropriate beam direction about the collimated light path 113 is selected in order to relay a collimated beam out of the microscope objective at a supercritical angle of incidence with respect to the cover-slip.

To fully homogenize and eliminate artifacts from the illumination, it is better to illuminate the specimen focal plane from all sides while maintaining the same inclination angle. This is accomplished by scanning collimated beam 205 in a circular path 202 about the optic axis 113. This collimated beam is relayed to the cover-slip as previously discussed.

Figure 3:
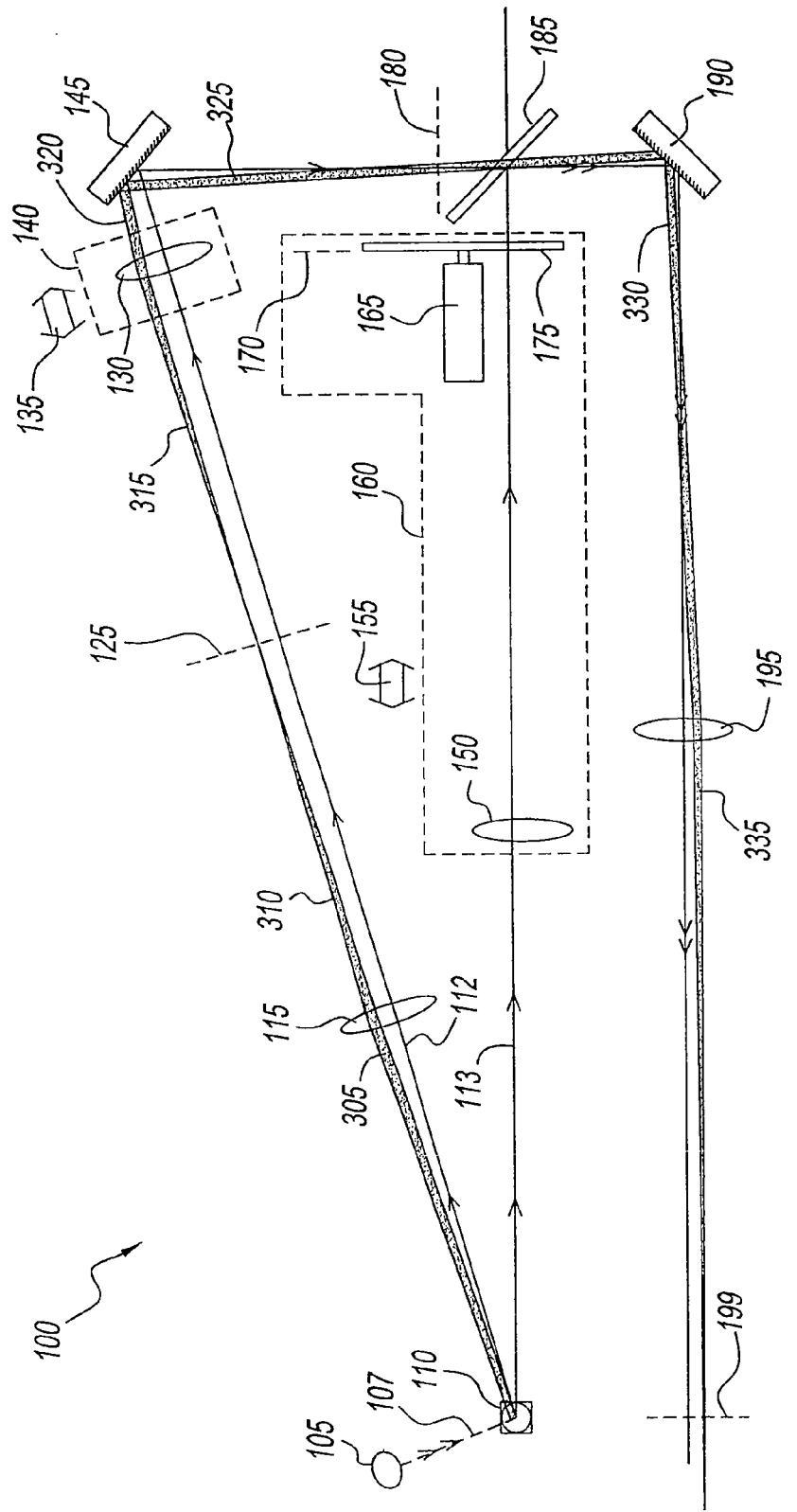
FIG. 3 is an illustration of the operation of the system of FIG. 1 in a mode of operation that projects a convergent light beam to a plane.

FIG. 3 is an illustration of the operation of system 100 in convergent mode. Light steering device 110 receives a light bundle from light source 105 and directs the light bundle to light path 112. The light bundle propagates from (a) light steering device 110 to lens 115 in a collimated beam 305, (b) through lens 115 to a plane 125 in a convergent beam 310, (c) from plane 125 to lens 130 in a divergent beam 315, (d) from lens 130 to mirror 145 in a collimated beam 320, (e) from mirror 145, through a plane 180, and through light steering device 185 to mirror 190 in a collimated beam 325, (f) from mirror 190 to lens 195 in a collimated beam 330, and (g) from lens 195 to plane 199 in a convergent beam 335. Lens 115, lens 130 and mirror 145 may be regarded as an optical subsystem that transforms the light bundle so that the light bundle is projected to plane 199 in convergent beam 335. Light steering device 110 controls a trajectory of the light bundle in light path 112 to steer convergent beam 335 to a target position in plane 199.

When system 100 is being used with a microscope for FRAP/photoactivation illumination, system 100 is in convergent mode and as such, light steering device 110 is set to direct light on or near light path 112. Directions on this optic axis correspond to bleaching locations at a center of the microscope field of view. Collimated beam 305 passes through lens 115 to become convergent beam 310, which comes to a focus at plane 125, and is re-collimated by lens 130. Lens 130 is on a translation mount that moves as indicated by an arrow 135, to enable a user to focus convergent beam 335 into the image plane of the microscope. This adjustment is independent of adjustments to the light path in the collimated mode (FIG. 2). Mirror 145 directs collimated beam 325 through a stationary pupil location at plane 180. The light then passes through light steering device 185, to mirror 190. Collimated beam 330 is received by lens 195 as an intermediate collimated light beam, and then focused by lens 195, as convergent beam 335, onto plane 199, which is located at the image plane of the microscope.

The pupil of light steering device 110 and the pupil of lens 115 are separated by the focal length of lens 115 such that the focus at plane 125 moves telecentricly. Similarly, plane 125 and lens 130 are separated by the focal length of lens 130, and lens 130 and lens 195 are separated by a distance equal to the sum of those focal lengths. Thus, system 100 has telecentric performance throughout.

During an experiment, a beam could be directed to a series of discrete locations within a field of view in plane 199, or it could be scanned in a raster motion to bleach an area. The position of the beam in plane 199 is dependent on an angle at which light is directed from light steering device 110 to light path 112 or light path 113. The motion would be controlled by a computer, and in a case where light source 105 is a laser, the laser power could be switched or otherwise modulated in conjunction with this if such a capability is implemented on the laser (e.g. using an AOTM).

Figure 4:
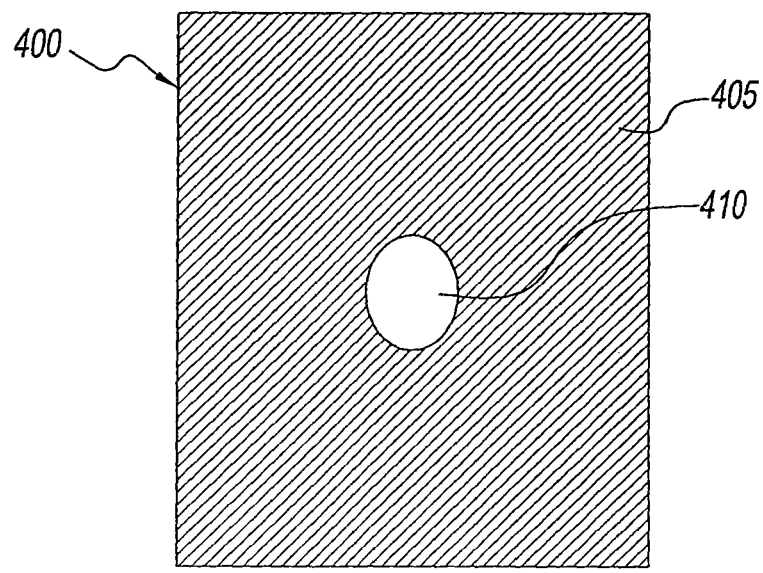
FIG. 4 is an illustration of an elliptical zone mirror.

As noted above, light steering device 185 may include an elliptical zone mirror (EZM). FIG. 4 is an illustration of an EZM 400 having a mirrored surface 405 and a clear aperture, i.e., an aperture 410, for a circular beam incident at 45 degrees. Consider a case of light steering device 185 being implemented with EZM 400. In the collimated mode of system 100 (see FIG. 2), the light bundle in divergent beam 215 is reflected by mirrored surface 405, and thereafter continues in divergent beam 220. In the convergent mode of system 100 (see FIG. 3), the light bundle in collimated beam 325 propagates from mirror 145, and passes through aperture 410 to mirror 190.

Referring again to FIG. 2, consider a case where steering device 185 is implemented with EZM 400, and system 100 is in collimated mode and being used for TIRF illumination. Note that aperture 410 does not affect the TIRF illumination since it is located near plane 170. Plane 170 is a conjugate plane to the entrance pupil of the objective lens. The TIRF illumination conditions require that the light be focused at the periphery of the objective lens aperture. Aperture 410 is sized so that divergent beam 215 does not strike aperture 410, but instead strikes mirrored surface 405.

Referring again to FIG. 3, consider a case where steering device 185 is implemented with EZM 400, and system 100 is in convergent mode and being used for FRAP illumination. Mirrored surface 405 has a minimal effect on the FRAP performance. Mirrored surface 405 is located near plane 180 at which collimated beam 325 is both on-axis and stationary. Aperture 410 limits the numerical aperture of the FRAP focus somewhat, but since in the experiments, regions are normally bleached, diffraction limited performance is not required.

Optical Variations

It should be noted that although a telecentric optical arrangement results in the optimal illumination conditions, it is not an absolute necessity. Practical implementations of the system will by necessity be imperfectly telecentric to accommodate the movement of optics for focusing, collimation adjustment, as well as the physical constraint of having two axis of light steering which may not occur at precisely the same location along the beam path.

Rapid switching of the illumination can be accomplished simply by directing the light bundle from light steering device 110 to a location other than the collimated beam path 113 or the converging beam path 112. The light could be directed to a beam dump placed at an intermediate position.

Diffuser 175 is used to increase the area of illuminate in the collimated mode. It should be noted that diffuser 175 is not an essential component to system 100 and most practical implementations will not require it.

EXAMPLE

Consider an example of a 60× objective with numerical aperture 1.45. Such a lens has the following parameters:

Beam acceptance aperture=8.7 mm. (assuming a 200 mm tube length)

Oil immersion index ($n_3$)=1.518

Tissue index ($n_1$)=1.38

Critical angle for TIRF=63.6 degrees (based on $n_1$ and $n_3$)

Critical diameter at objective pupil (aperture)=8.16 mm

For such a lens the diameter of aperture 410 could be 5 mm. This would allow a 3 mm FRAP beam some scanning room (since EZM 400 is not located exactly at the pupil at plane 170). The TIRF beams have some room for divergence after the focal point, and can still illuminate at sub-critical (<8.16 mm), critical (8.16 mm) and supercritical (>8.16) positions. These relationships assume that lens 195 has equal focal length to the tube lens of the microscope such that the magnification of the combined relay telescope is 1. Otherwise, a scaling factor should be applied.

Calibration of Galvanometer Positions

This discussion assumes that a CCD or other camera is being used to monitor an experiment and that the images from that camera are available for analysis.

Galvo and CCD Parameters

Galvanometer position coordinates: $(G_x, G_y)$
CCD camera position coordinates: $(C_x, C_y)$
FRAP Transform Coordinates:
Galvo Origin Position: $(G_{x0}, G_{y0})$
Galvo position derivatives: $(G_x dC_x, G_y dC_x)$, $(G_x dC_y, G_y dC_y)$ Transforms from CCD camera coordinates to Galvo coordinates for FRAP $$G_x = G_{x0} + (G_x dC_x, G_x dC_y) \cdot (C_x, C_y)$$

$$G_y = G_{y0} + (G_x dC_x, G_y dC_y) \cdot (C_x, C_y)$$

TIRF Transform Coordinates:
Galvo coordinates for TIRF axis: $(T_{x0}, T_{y0})$

Automated Calibration of FRAP Galvanometer Positions

A simple linear transform can be used to convert from camera coordinates $(C_x, C_y)$ to galvanometer coordinates $(G_x, G_y)$. The calibration is well suited to automation or by a simple user driven procedure.

Using image analysis to provide feedback of the focused spot position on the CCD camera the spot could be directed to the origin position (probably the center of the CCD or the corner) and those coordinates recorded as $(G_{x0}, G_{y0})$. Next the galvo could be driven (with feedback) to a position located horizontally with respect to the origin $(dC_y=0)$ to calculate the X-axis position derivatives $(G_x dC_x, G_y dC_x)$. Similarly, using a position located vertically with respect to the origin $(dC_x=0)$ the Y-axis position derivatives $(G_x dC_y, G_y dC_y)$ could be determined.

This technique would require a specimen to be in focus and that the focused spot to be visible. The image analysis used to locate the spot could use the intensity maxima, or possibly a two dimensional centroid calculation.

Automated Calibration of TIRF Galvanometer Positions

The TIRF galvo calibration is complicated by the fact that the beam is not focused in the specimen focal plane and as such cannot be located directly. The most useful feedback mechanism would be overall image brightness. This is based on the observation that the due to the deeper illumination penetration, specimens are illuminated brighter under epi-illumination conditions than under TIRF illumination. This is particularly true for aqueous fluorescent liquid specimens that have even fluorescence from the cover slip surface outward. Another useful specimen would be a glass cover slip uniformly coated with quantum dots or another thin fluorescent coating. Using such a calibration specimen, a calibration algorithm can be automated.

The total integrated image intensity is used as feedback. This is appropriate for all galvanometer locations near the TIRF light path since the diffuser 175 fills the entire field of view. If a raster scan was made of all the galvanometer locations near the TIRF light path axis, the resultant image would be a bright filled circle with a sharp drop off to darker values outside a radius corresponding to the critical illumination angle. The center of the circle would correspond to the galvanometer coordinates of the TIRF light path axis $(T_{x0}, T_{y0})$.

The total integrated image intensity can be measured either by numerically summing the pixels of an image recorded by a camera, or by placing a light detector near a conjugate plane to the microscope objective pupil to directly measure total specimen fluorescence across a wide field.

Figure 5:
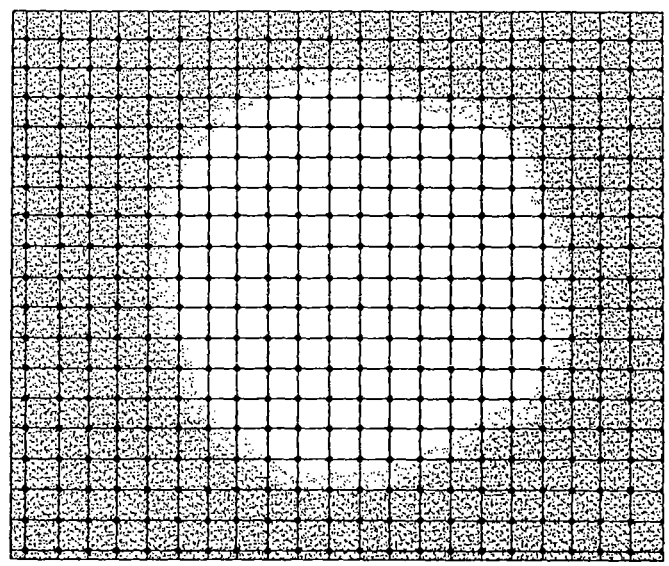
FIG. 5 is a rough grid scan using a whole image integrated intensity as an indicator of the incidence angle of a collimated beam.

FIG. 5 illustrates how measuring the whole field's integrated intensity at points on a coarse grid of galvanometer locations can be used to indicate which galvanometer locations generate sub-critical, critical and supercritical illumination conditions.

Once the center of the circle is located roughly it can be more accurately located by sampling along trajectories radiating outward from the center. These trajectories can be used to identify the critical angle location $(G_x, G_y)$ precisely either using a threshold measure or by locating the position with maximum slope. With this information very accurate TIRF imaging trajectories can be designed. These would take the form of circles centered on the TIRF light path axis $(T_{x0}, T_{y0})$ with different radii depending on the desired depth penetration, or even epi-illumination.

Figure 6:
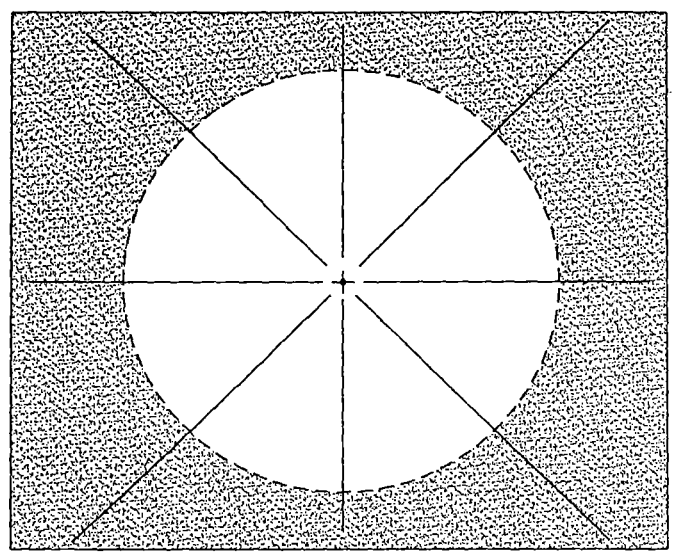
FIG. 6 is an illustration showing that slowly scanning galvanometers along certain trajectories could be used to identify a critical angle.

FIG. 6 is an illustration showing that slowly scanning the galvanometers along the trajectories shown (solid lines) away from the rough center (cross hair) while measuring the whole field integrated image intensity, could be used to identify the set of galvo positions resulting in illumination through the microscope objective at the critical angle (circle shown with dotted line).

Figure 7:
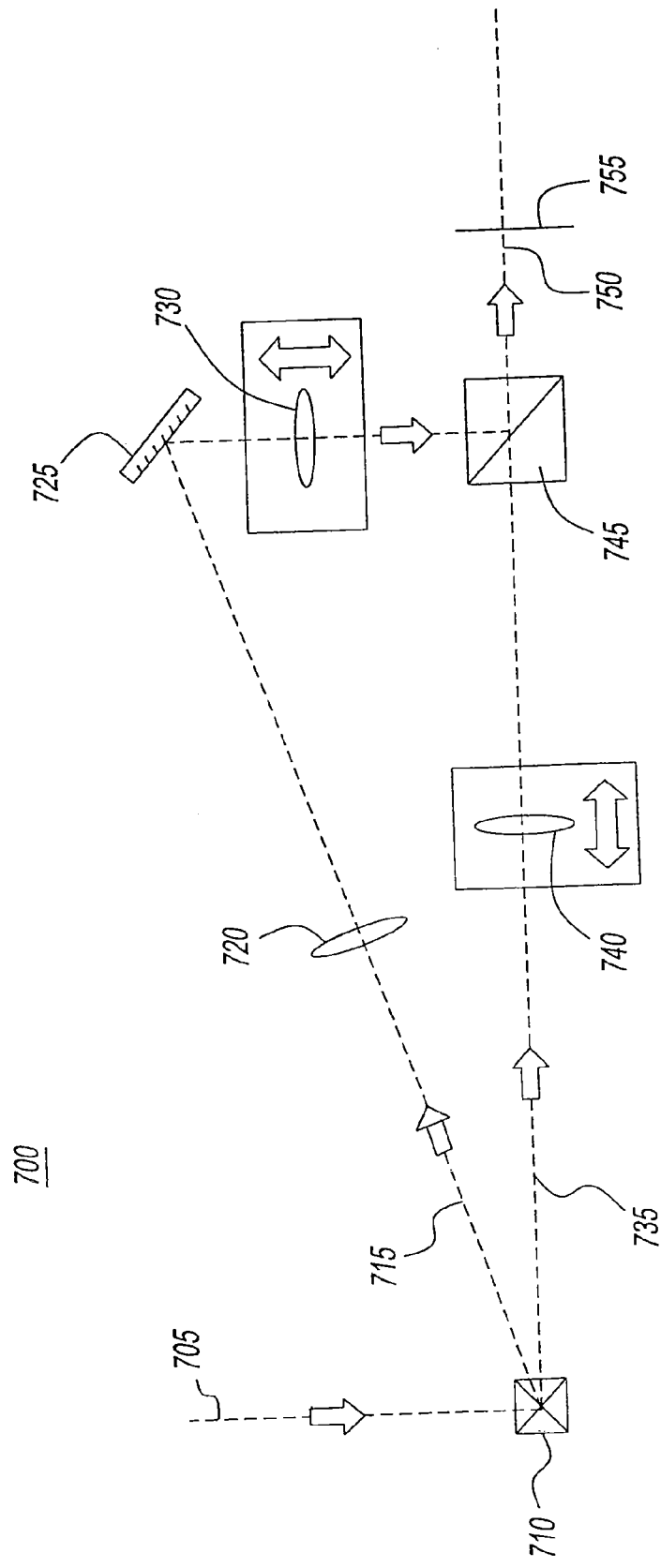
FIG. 7 is a block diagram of an illumination system.

FIG. 7 is a block diagram of an illumination system, i.e., system 700, that, similarly to system 100 that has a collimated mode of operation that projects a collimated light beam to a plane 755, and a convergent mode of operation that projects a convergent light beam to plane 755. System 700 includes a light steering device 710, lenses 720, 730 and 740, a mirror 725, and a light steering device 745.

Light steering device 710 is similar in functionality to light steering device 110, and can be implemented similarly to light steering device 110. Light steering device 745 is similar in functionality to light steering device 185, and can be implemented similarly to light steering device 185, but is shown in system 700 as being a beam cube.

In the collimated mode of operation of system 700, light steering device 710 receives a light bundle via a light path 705, and directs the light bundle to a light path 715. Light path 715 runs from light steering device 710, through lens 720, to mirror 725, through lens 730 to light steering device 745. Light steering device 745 receives the light bundle via light path 715 and directs the light bundle to a downstream light path, i.e., a light path 750.

In the convergent mode of operation of system 700, light steering device 710 receives a light bundle via light path 705, and directs the light bundle to a light path 735. Light path 735 runs from light steering device 710, through lens 740, to light steering device 745. Light steering device 745 receives the light bundle via light path 735, and directs the light bundle to light path 750.

Lens 740 is moveable, along a portion of light path 735, to adjust focus. Lens 730 is moveable, along a portion of light path 715, to adjust collimation.

Figure 8:
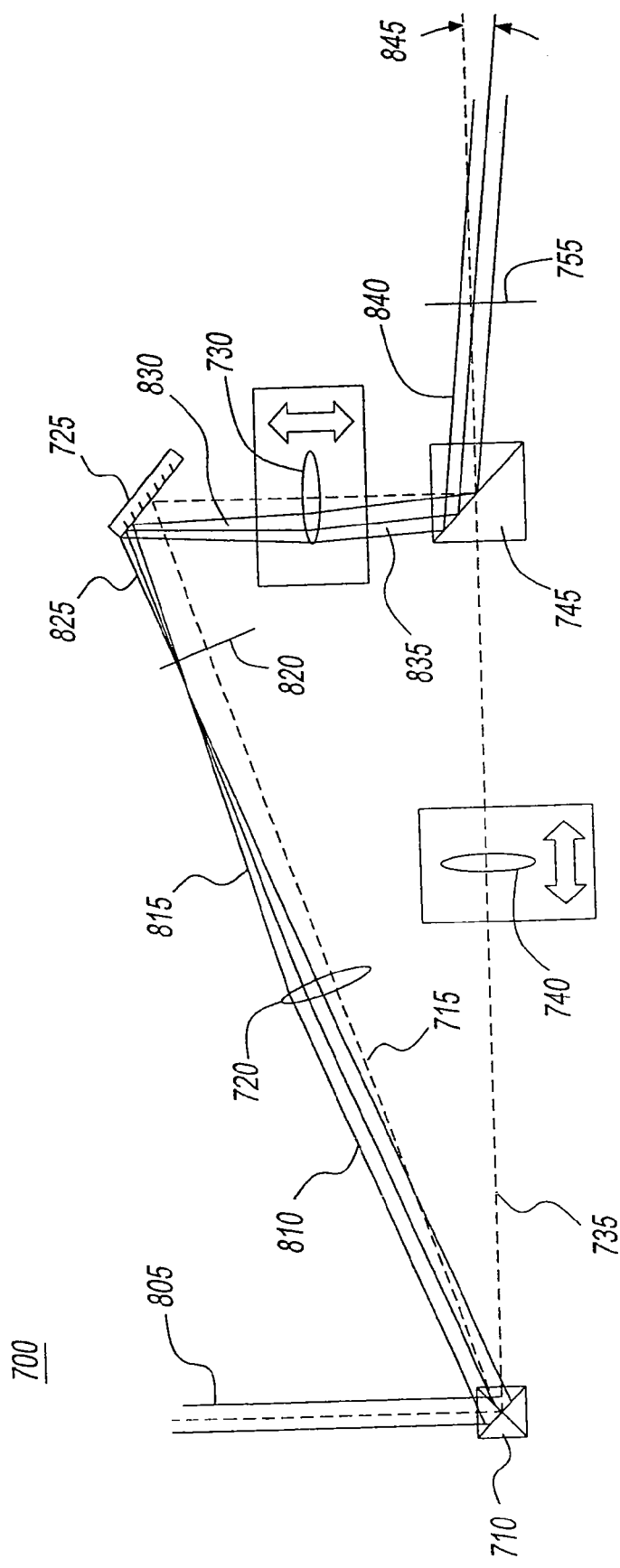
FIG. 8 is an illustration of the operation of the system of FIG. 7 in a mode that projects a collimated light beam to a plane.

FIG. 8 is an illustration of the operation of system 700 in collimated mode. Light steering device 710 receives a light bundle in a collimated beam 805, and directs the light bundle to lens 720 in a collimated beam 810. Lens 720 receives the light bundle in collimated beam 810, and directs it, in a convergent beam 815, to a plane 820. From plane 820, the light bundle propagates to mirror 725 in a divergent beam 825. The light bundle propagates from mirror 725 to lens 730 in a divergent beam 830. Lens 730 receives the light bundle in divergent beam 830, and directs it to light steering device 745 in a collimated beam 835. Light steering device 745 receives the light bundle in collimated beam 835, and directs it to plane 755 in a collimated beam 840. Lens 720, mirror 725 and lens 730 may be regarded as an optical subsystem that transforms the light bundle so that the light bundle is projected to plane 755 in collimated beam 840. Light steering device 710 controls a trajectory of the light bundle in light path 715 to steer collimated beam 840 through plane 755 at a designated incident angle 845.

Figure 9:
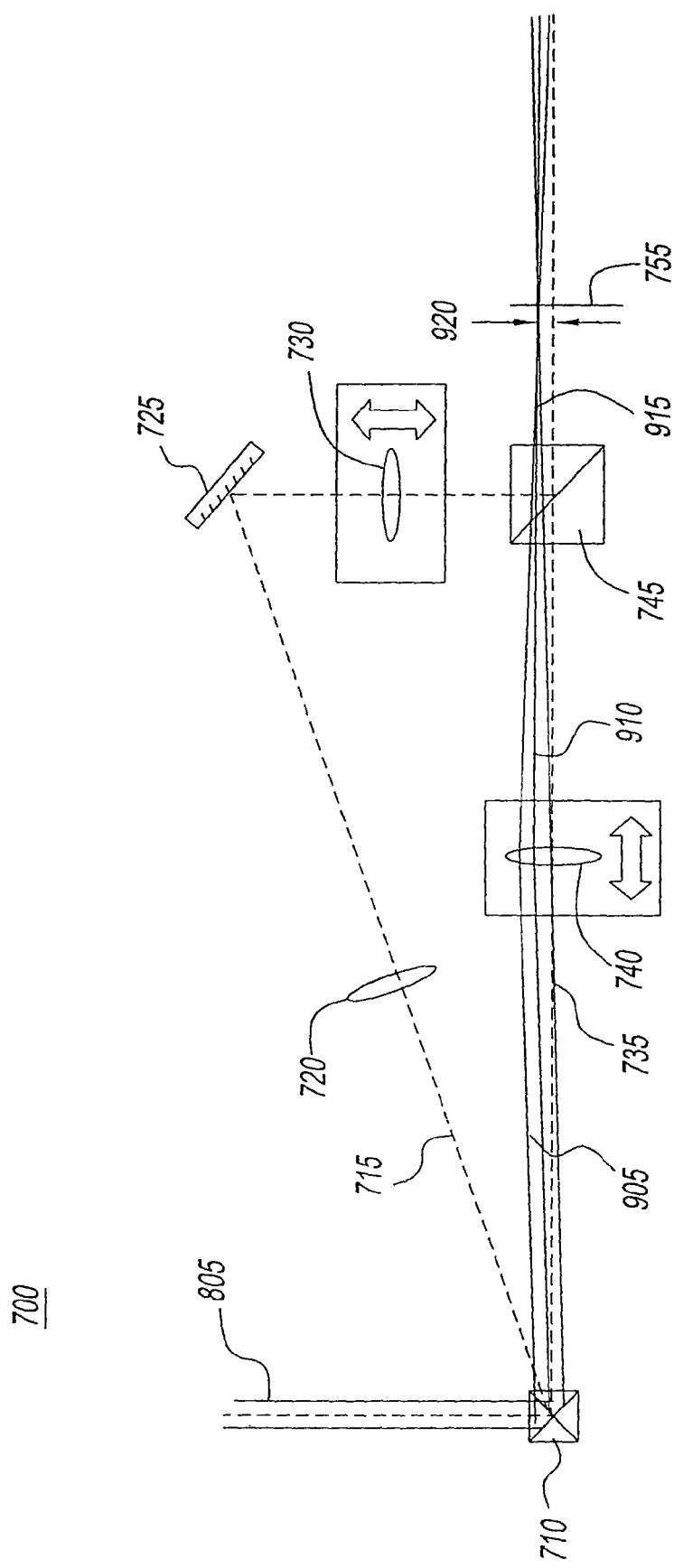
FIG. 9 is an illustration of the operation of the system of FIG. 7 in a mode that projects a convergent light beam to a plane.

FIG. 9 is an illustration of the operation of system 700 in convergent mode. Light steering device 710 receives a light bundle in collimated beam 805, and directs the light bundle to lens 740 in a collimated beam 905. The light bundle propagates from lens 740 to light steering device 745 in a convergent beam 910, and through light steering device 745 to plane 755 in a convergent beam 915. Lens 740 may be regarded as an optical subsystem that transforms the light bundle so that the light bundle is projected to plane 755 in convergent beam 915. Light steering device 710 controls a trajectory of the light bundle in light path 735 to steer convergent beam 915 to a target position (for example, at an xy coordinate indicated in FIG. 9 by an offset 920) in plane 755.

Figure 10:
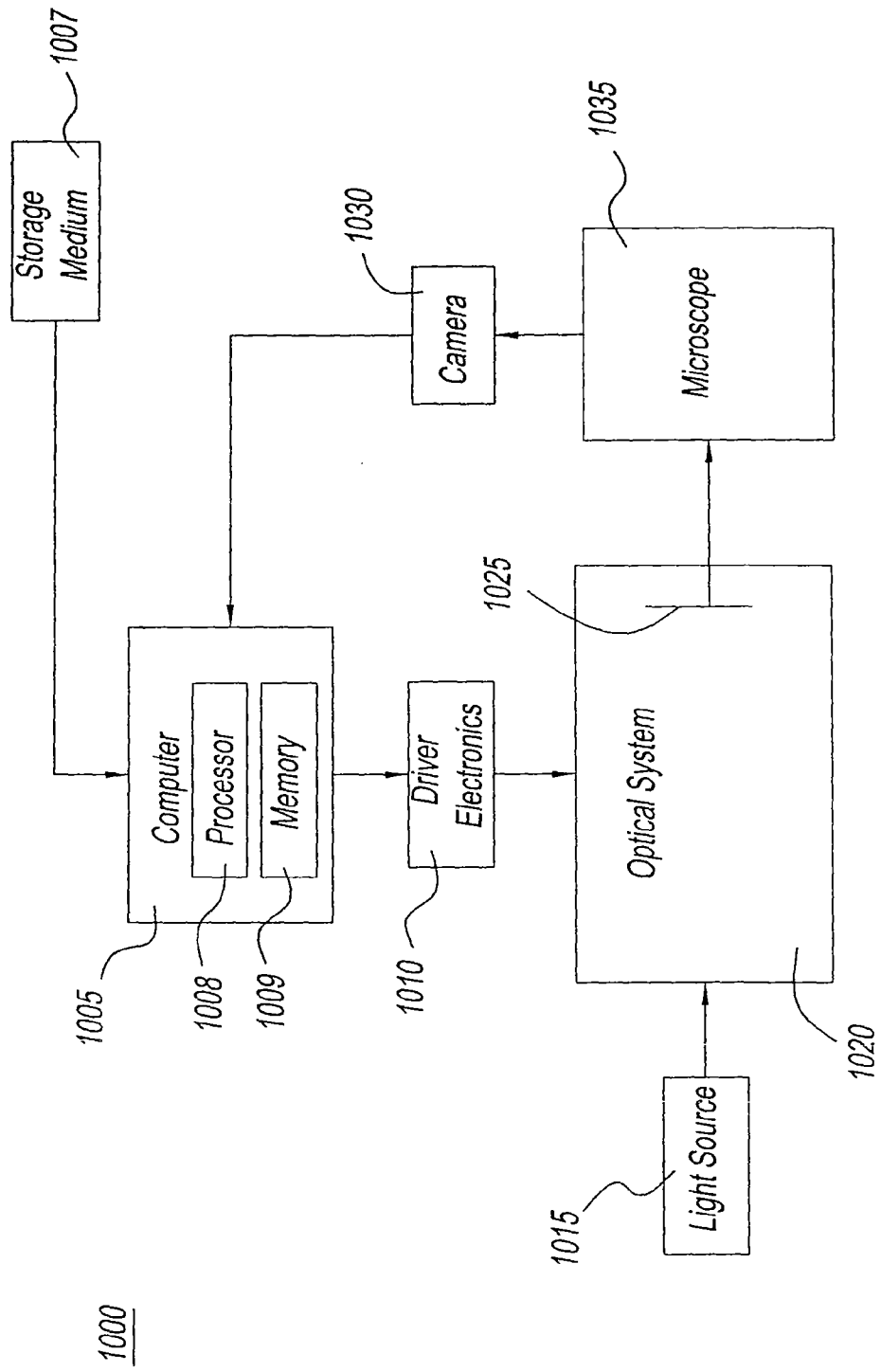
FIG. 10 is a block diagram of a system for microscopy.

FIG. 10 is a block diagram of a system 1000 for microscopy. System 1000 includes a light source 1015, an optical system 1020, a microscope 1035, a camera 1030, a computer 1005, and driver electronics 1010.

Light source 1015, e.g., a laser, emits light. Optical system 1020 receives the light from light source 1015, modifies the light and illuminates a plane 1025 with either of a collimated light beam or a convergent light beam. Optical system 1020 may be implemented, for example, by either of system 100 or system 700. Plane 1025 coincides with an image plane of microscope 1035. Microscope 1035 produces an image of a specimen situated in plane 1025. Camera 1030 is an imaging apparatus that converts the image from microscope 1035 into an image in a digital data format that is processed by computer 1005. Computer 1005 evaluates the image, and provides a signal to driver electronics 1010, which in turn controls optical system 1020.

Computer 1005 evaluates a characteristic of the image, for example, a physical feature in the image, or a quality of the image that is indicative of its focus. Based on the characteristic, computer 1005 performs calculations for, ultimately, controlling the illumination in plane 1025. For example, in a case where system 1000 is being employed to illuminate plane 1025 with a collimated light beam, computer 1005 performs calculations for controlling a light steering device within optical system 1020 to steer the collimated light beam through plane 1025 at a designated incidence angle. Similarly, in a case where system 1000 is being employed to illuminate plane 1025 with a convergent light beam, computer 1005 performs calculations for controlling the light steering device within optical system 1020 to steer the convergent light beam to a target position in plane 1025. Computer 1005 also controls positioning of lenses within optical system 1020 to focus the light beams. For examples of some of the calculations performed by computer 1005, see the discussions above concerning (a) calibration of galvanometer positions, (b) automated calibration of FRAP galvanometer positions, and (c) automated calibration of TIRF galvanometer positions.

Computer 1005 includes a processor 1008 and a memory 1009 that contains instructions that are executable by processor 1008. Upon execution of the instructions, processor 1008 performs methods that include the evaluation of the characteristic of the image, the calculations of settings for controlling optical system 1020, and thus the ultimate control of optical system 1020 to perform methods that include the various operations described herein.

Although system 1000 is described herein as having the instructions for processor 1008 installed into memory 1009, the instructions can be tangibly embodied on an external computer-readable storage medium, e.g., a storage medium 1007, for subsequent loading into memory 1009. Storage medium 1007 can be any conventional storage medium, including, but not limited to, a floppy disk, a compact disk, a magnetic tape, a read only memory, or an optical storage medium. The instructions could also be embodied in a random access memory, or other type of electronic storage, located on a remote storage system and coupled to memory 1007.

Moreover, although computer 1005 is described herein as having the instructions installed in memory 1009, and therefore being implemented in software, the operation of computer 1005 could be implemented in any of hardware, firmware, software, or a combination thereof.

System 1000 creates optimal illumination conditions for total internal reflection fluorescent (TIRF) microscopy. The illumination is uniform across a large field of view, does not have the interference fringes seen in other illumination systems, and the penetration depth of the evanescent wave can be very rapidly varied. System 1000 creates illumination conditions for fluorescence recovery after photobleaching (FRAP) or photoactivation experiments.

The quality of TIRF illumination that system 1000 produces is superior to systems that use stationary beams. The systems that use stationary beams suffer from interference fringes, flaring, shadowing and other types of non-uniformity. System 1000, by scanning the beam in a trajectory of beams with equal inclination angles, averages out such artifacts.

System 1000 allows the illumination angle of the incident beam to be varied in milliseconds or less, and provides an extremely rapid method for achieving multi-angle TIRF microscopy over a large range of incident angles. Computer 1005 will use an automated search algorithm, with feedback control, to automatically optimize TIRF conditions for many types of objectives and dichroic filter cubes.

FRAP/Photoactivation TIRF and the Objective Lens

FRAP experiments require selected regions of a specimen being observed to be photobleached. Conclusions can be made about the dynamics of molecules by monitoring the kinetics and extent of fluorescence recovery after FRAP experiments and by examining the spatial pattern of fluorescence recovery. A correlate approach is to photoactivate dyes or molecules either so as either to manipulate the cellular milieu (e.g. releasing caged calcium, etc.) or to track the cellular fate of photoactivated molecules, which may through photoactivation be brighter or have an altered spectral characteristics.

Since the bleaching/photoactivation must be localized to a region of interest, it is commonly accomplished by scanning a focused beam of light across a region of interest using a raster scan or other area-covering beam trajectory. Alternatively, FRAP may be achieved using selective illumination with epifluorescent light that is passed through an adjustable mask (e.g. a rectangle of adjustable width and height) at a conjugate image plane. While less expensive, the latter is slow to adjust as it's typically done manually and bleaching/photoactivating small objects, multiple objects, or other shapes (e.g. a circle) is not possible. Thus, for speed and flexibility a raster scanned approach is generally preferred.

Generally the area bleached is a sub-region of area observed so that both are positioned at the focal plane of the microscope objective. This specimen focal plane has corresponding image planes at the image plane in the observation beam path of the microscope and also on the excitation beam path (in most microscopes).

Different Requirements for FRAP/Photoactivation Versus TIRF Illumination.

For FRAP/photoactivation experiments a scanned beam (or mask) must be focused on an image plane of the microscope. The size of the smallest FRAP/photoactivated point is determined by the wavelength of the illuminating light, the numerical aperture (NA) of the objective and the extent to which the back focal plane of the objective is filled. The microscope optics (including the objective lens) relays this focus to the specimen image plane. Assuming the scanning optics are telecentric and the objective is infinity corrected the light will pass through the center of the microscope objective lens pupil as a collimated beam.

For TIRF illumination a collimated beam is required at the specimen image plane. Unlike FRAP, for TIRF illumination the laser beam must be focused on the outer rim of the back focal plane of the objective lens. For TIR to occur two criteria must be met: (i) light must go from medium of high refractive index (typically glass) to lower refractive index (e.g. aqueous medium, cell cytosol, etc.) and (ii) the incidence angle of the light with respect to the optical axis (normal) must be greater than the critical incidence angle for the specimen—coverslip interface being observed. For the latter these high incidence angle foci occur near the outer perimeter of the pupil aperture. If a collimated beam is incident at the image plane of the microscope it is relayed to the specimen image plane. At the pupil of the objective lens this light will come to a sharp focus.

System 1000 can be used in applications such as (a) multi-angle TIRF microscopy, (b) FRAP in combination with TIRF, (c) photoactivation in combination with TIRF, (d) optical trapping in combination with TIRF, (e) in vitro or in vivo imaging, and (f) material science and local activation of a surface, e.g., for lithography.

The techniques described herein are exemplary, and should not be construed as implying any particular limitation on the present invention. It should be understood that various alternatives, combinations and modifications could be devised by those skilled in the art. The present invention is intended to embrace all such alternatives, modifications and variances that fall within the scope of the appended claims.

What is claimed is:

1. A method comprising:
   projecting a collimated light beam from an optical system to a plane during a first mode of operation of said optical system; and
   projecting a convergent light beam from said optical system to said plane during a second mode of operation of said optical system,
   wherein said projecting said collimated light beam comprises:
      routing a first light bundle from a light source to an orthogonal pair of galvanometer scanning mirrors; and
      controlling said orthogonal pair of galvanometer scanning mirrors to:
         (a) direct said first light bundle to a first light path in said optical system along which said first light bundle propagates to produce said collimated light beam; and
         (b) control a trajectory of said first light bundle in said first light path to steer said collimated light beam through said plane at a designated incidence angle, and
   wherein said projecting said convergent light beam comprises:
      routing a second light bundle from said light source to said orthogonal pair of galvanometer scanning mirrors; and
      controlling said orthogonal pair of galvanometer scanning mirrors to:
         (a) direct said second light bundle to a second light path in said optical system along which said second light bundle propagates to produce said convergent light beam; and
         (b) control a trajectory of said second light bundle in said second light path to steer said convergent light beam to a target position in said plane.

2. The method of claim 1, further comprising:
   (i) during said first mode of operation:
      (a) receiving said first light bundle at an optical device comprising a mirror having an aperture therethrough, via said first light path; and
      (b) reflecting said first light bundle from said mirror to a downstream light path that leads to said plane; and
   (ii) during said second mode of operation:
      (a) receiving said second light bundle at said optical device via said second light path; and
      (b) passing said second light bundle through said aperture to a downstream light path that leads to said plane.

3. The method of claim 1,
   wherein said projecting said collimated light beam comprises routing said first light bundle in a divergent light beam to a lens that transforms said divergent light beam into said collimated light beam, and
   wherein said projecting said convergent light beam comprises routing said second light bundle in an intermediate collimated light beam to said lens, wherein said lens transforms said intermediate collimated light beam into said convergent light beam.

4. The method of claim 1, wherein said first mode of operation is employed in conjunction with a process selected from the group consisting of (a) total internal reflection fluorescent illumination, and (b) evanescent field fluorescence recovery after photobleaching illumination.

5. The method of claim 1, wherein said second mode of operation is employed in conjunction with a process selected from the group consisting of (a) fluorescence recovery after photobleaching illumination, (b) photoactivation illumination, (c) photobleaching illumination, (d) an optical tweezers operation, and (e) an optical uncaging operation.

6. The method of claim 1, wherein said plane coincides with an image plane of a microscope.

7. An apparatus comprising:
   an optical system that:
      projects a collimated light beam to a plane during a first mode of operation of said optical system; and
      projects a convergent light beam to said plane during a second mode of operation of said optical system,
   wherein said optical system comprises:
      a first light path along which a first light bundle propagates during said first mode of operation to produce said collimated light beam;
      a second light path along which a second light bundle propagates during said second mode of operation to produce said convergent light beam; and an orthogonal pair of galvanometer scanning mirrors that:
(i) during said first mode of operation:
(a) receives said first light bundle from a light source;
(b) directs said first light bundle to said first light path; and
(c) controls a trajectory of said first light bundle in said first light path to steer said collimated light beam through said plane at a designated incidence angle; and
(ii) during said second mode of operation:
(a) receives said second light bundle from said light source;
(b) directs said second light bundle to said second light path; and
(c) controls a trajectory of said second light bundle in said second light path to steer said convergent light beam to a target position in said plane.

8. The apparatus of claim 7,
wherein said optical system further comprises an optical device comprising a mirror having an aperture therethrough, that:
during said first mode of operation, receives said first light bundle via said first light path, and reflects said first light bundle from said mirror to a downstream light path that leads to said plane; and
during said second mode of operation, receives said second light bundle via said second light path, and passes said second light bundle through said aperture to a downstream light path that leads to said plane.

9. The apparatus of claim 7, wherein said optical system further comprises a lens that:
during said first mode of operation, receives said first light bundle in a divergent light beam, and directs said first light bundle in said collimated light beam, and
during said second mode of operation, receives said second light bundle in a collimated light beam, and directs said second light bundle in said convergent light beam.

10. The apparatus of claim 7, wherein said first mode of operation is employed in conjunction with a process selected from the group consisting of (a) total internal reflection fluorescent illumination, and (b) evanescent field fluorescence recovery after photobleaching illumination.

11. The apparatus of claim 7, wherein said second mode of operation is employed in conjunction with a process selected from the group consisting of (a) fluorescence recovery after photobleaching illumination, (b) photoactivation illumination, (c) photobleaching illumination, (d) an optical tweezers operation, and (e) an optical uncaging operation.

12. The apparatus of claim 7, wherein said plane coincides with an image plane of a microscope.

13. A system comprising:
a first optical subsystem;
a second optical subsystem; and
an orthogonal pair of galvanometer scanning mirrors that:
(i) during a first mode of operation:
(a) receives a first light bundle from a light source;
(b) directs said first light bundle to a first light path in said first optical subsystem; and
(c) controls a trajectory of said first light bundle in said first light path to steer said first light bundle through a plane at a designated incidence angle; and
(ii) during a second mode of operation:
(a) receives a second light bundle from said light source;
(b) directs said second light bundle to a second light path in said second optical subsystem; and
(c) controls a trajectory of said second light bundle in said second light path to steer said second light bundle to a target position in said plane,
wherein said first optical subsystem transforms said first light bundle so that said first light bundle is projected to said plane in a collimated light beam; and
wherein said second optical subsystem transforms said second light bundle so that said second light bundle is projected to said plane in a convergent light beam.

14. The system of claim 13, further comprising:
a microscope,
wherein said plane coincides with an image plane of said microscope.

15. The system of claim 14, further comprising:
a imaging apparatus that produces an image of a specimen in said image plane;
a processor that evaluates a characteristic of said image, and based thereon, produces a control signal that:
during said first mode of operation, controls said orthogonal pair of galvanometer scanning mirrors to control said trajectory of said first light bundle; and
during said second mode of operation, controls said orthogonal pair of galvanometer scanning mirrors to control said trajectory of said second light bundle.

16. The system of claim 13, wherein said first mode of operation is employed in conjunction with a process selected from the group consisting of (a) total internal reflection fluorescent illumination, and (b) evanescent field fluorescence recovery after photobleaching illumination.

17. The system of claim 13, wherein said second mode of operation is employed in conjunction with a process selected from the group consisting of (a) fluorescence recovery after photobleaching illumination, (b) photoactivation illumination, (c) photobleaching illumination, (d) an optical tweezers operation, and (e) an optical uncaging operation.

18. The system of claim 13, further comprising an optical device comprising a mirror having an aperture therethrough, that:
during said first mode of operation, receives said first light bundle via said first light path, and reflects said first light bundle from said mirror to a downstream light path that leads to said plane; and
during said second mode of operation, receives said second light bundle via said second light path, and passes said second light bundle through said aperture to a downstream light path that leads to said plane.

19. A system, comprising:
a first optical subsystem;
a second optical subsystem;
a light steering device that:
(i) during a first mode of operation:
(a) receives a first light bundle from a light source; and
(b) directs said first light bundle to a first light path in said first optical subsystem; and
(ii) during a second mode of operation:
(a) receives a second light bundle from said light source; and
(b) directs said second light bundle to a second light path in said second optical subsystem; and
an optical device comprising a mirror having an aperture therethrough, that:
(i) during said first mode of operation, receives said first light bundle via said first light path, and reflects said first light bundle from said mirror to a downstream light path that leads to a plane; and (ii) during said second mode of operation, receives said second light bundle via said second light path, and passes said second light bundle through said aperture to a downstream light path that leads to said plane, wherein said first optical subsystem transforms said first light bundle so that said first light bundle is projected to said plane in a collimated light beam; and wherein said second optical subsystem transforms said second light bundle so that said second light bundle is projected to said plane in a convergent light beam.

20. The system of claim 19, wherein said light steering device:
   (i) during said first mode of operation, controls a trajectory of said first light bundle in said first light path to steer said first light bundle through said plane at a designated incidence angle, and
   (ii) during said second mode of operation, controls a trajectory of said second light bundle in said second light path to steer said second light bundle to a target position in said plane.

21. The system of claim 20, wherein said light steering device comprises an orthogonal pair of galvanometer scanning mirrors.

* * * * *